(12) United States Patent
Borg et al.

(10) Patent No.: US 9,375,159 B2
(45) Date of Patent: Jun. 28, 2016

(54) DEVICE FOR INDICATOR DILUTION MEASUREMENTS

(75) Inventors: Ulf Borg, Longmont, CO (US); Reinhold Knoll, Munich (DE); Frederic Michard, Gex (FR); Ulrich Pfeiffer, Munich (DE)

(73) Assignee: Edwards Lifesciences IPRM AG, Nyon (CH)

( * ) Notice: Subject to any disclaimer, the term of this patent is extended or adjusted under 35 U.S.C. 154(b) by 814 days.

(21) Appl. No.: 12/738,073

(22) PCT Filed: Oct. 15, 2008

(86) PCT No.: PCT/EP2008/008722
§ 371 (c)(1),
(2), (4) Date: Dec. 8, 2010

(87) PCT Pub. No.: WO2009/049872
PCT Pub. Date: Apr. 23, 2009

(65) Prior Publication Data
US 2011/0105911 A1    May 5, 2011

(30) Foreign Application Priority Data
Oct. 15, 2007    (DE) .......................... 10 2007 049 409

(51) Int. Cl.
*A61B 5/02* (2006.01)
*A61B 5/029* (2006.01)
*A61B 5/028* (2006.01)
*A61B 5/0275* (2006.01)

(52) U.S. Cl.
CPC ................. *A61B 5/029* (2013.01); *A61B 5/028* (2013.01); *A61B 5/02755* (2013.01)

(58) Field of Classification Search
CPC ........... A61B 5/02; A61B 5/029; A61B 5/028
USPC ..................................... 600/481–50
See application file for complete search history.

(56) References Cited

U.S. PATENT DOCUMENTS

| 5,526,817 A | 6/1996 | Pfeiffer et al. |
| 6,061,590 A * | 5/2000 | Krivitski ........................ 600/431 |

(Continued)

FOREIGN PATENT DOCUMENTS

| WO | 2006087245 | 8/2006 |
| WO | WO 2006/087245 A1 * | 8/2006 ............. A61B 5/029 |

OTHER PUBLICATIONS

International Search Report, Mar. 3, 2009.
(Continued)

*Primary Examiner* — Patricia Mallari
*Assistant Examiner* — Eric Messersmith
(74) *Attorney, Agent, or Firm* — Michael Crapenhoft

(57) ABSTRACT

The invention relates to indicator dilution measurements of a central volume (V1) with a first site of injection (S1) upstream of the central volume (V1) a second site of detection (S2) of the diluted indicator downstream of the central volume (V1), wherein a first additional volume (V2) is defined between the first site (S1) and the central volume (V1) and a first additional branch (B2) is defined between the first site (S1) and the central volume (V1) and wherein a second additional volume (V3) is defined between the central volume (V1) and the second site (S2) and a second additional branch (B3) is defined between the central volume (V1) and the second site (S2) wherein a result of central volumetric parameters are corrected for the first and second additional volumes (V2, V3) and/or for the first and second additional branches (B2, B3).

4 Claims, 6 Drawing Sheets

(56) References Cited

U.S. PATENT DOCUMENTS

Figure 1:
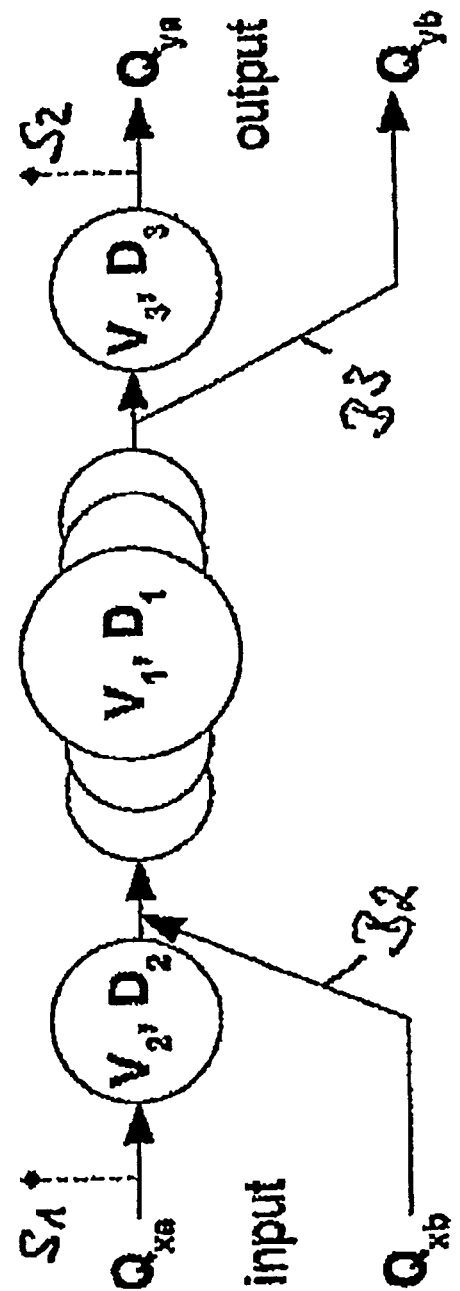

2003/0158491 A1* 8/2003 Krivitski .............. A61B 5/6855
  600/505
2008/0146945 A1* 6/2008 Pfeiffer et al. ................ 600/484

OTHER PUBLICATIONS

Korean Office Action translation, Nov. 11, 2014.
Chinese Office Action, Jul. 26, 2011.

* cited by examiner

DEVICE FOR INDICATOR DILUTION MEASUREMENTS

The present application is a U.S. National Phase of International Patent Application No. PCT/EP2008/008722, which was filed Oct. 15, 2008, which claims the benefit of priority of DE 10 2007 049 409.4, which was filed Oct. 15, 2007. Each of these applications is incorporated by reference in its entirety.

The invention relates to a method and a device for indicator dilution measurements. Especially, the invention relates to a method and an apparatus for volumetric physiological monitoring.

Indicator dilution measurements are often performed with multiple input and multiple output branches. For instance, in a thermodilution measurement the injectate is introduced into the blood stream in the superior vena cava and is subsequently mixing with the blood stream from the inferior vena cava when entering the right ventricle. Another example is the situation when the blood temperature is recorded downstream in the femoral artery after the blood stream has been branching into several arterial vessels. This procedure will not change the result of the calculation of a central volume of interest as long as the volumes and delays caused by the afferent and efferent branches are negligible. However, in case there are significant volumes and delays within the various branches significant errors are introduced.

In particular, the measurement of cardiac output (CO) and global end-diastolic volume (GEDV) has become an established method for monitoring and management of hemodynamics and volume status in critically ill patients and patients under increased risk of physiological derangement.

In order to conduct a measurement, a cold bolus of an isotonic solution (e.g. 15 ml of 0.9% saline iced or at room temperature) is currently injected through a central venous catheter. This catheter is usually placed with its tip in the superior vena cava close to the right atrium (jugular or subclavian venous catheter). After central venous injection, the cold indicator mixes with blood and dilutes in the largest accessible volumes while travelling through the cardiopulmonary system.

In addition, the thermal indicator is not strictly bound to the intravascular area or space but, dependent on time and available surface, also enters the extravascular space in the lungs in a manner which is dependent on vascular exchange surface (which is by far largest in the capillary system of the lungs), heat capacity and thermal conductivity of the extravascular structures. Since the extravascular structures of the lungs are composed of more than 80% water, the cold indicator mainly diffuses into and penetrates these spaces via convection and diffusion. The warm blood following (subsequent to) the cold bolus again washes out the cold indicator from the pulmonary extravascular space. In this way the cold indicator perfectly mixes with cardiopulmonary blood volume and extravascular lung water, but also with the blood volume of the large afferent and efferent blood vessels, the sum of which is called intrathoracic thermal volume (ITTV).

In the vast majority of patients the resulting transpulmonary thermodilution curve is recorded via a thermistor-tipped catheter in the femoral artery.

From this thermodilution curve, the cardiac output CO is calculated applying the conventional Stewart-Hamilton algorithm.

From indicator dilution principles, it is known that in a tubing system with multiple inflows but with a unique mainstream with several mixing chambers in series and multiple outflows the volume of the mainstream compartment can be calculated by the product of mean transit time (MTt) and flow, whereas the volume of the largest mixing chamber in the mainstream compartment may be calculated from the product of the exponential downslope time (DSt) multiplied by flow.

By applying these principles, the following volumes may be calculated by transpulmonary thermodilution:

$$ITTV = MTt \cdot CO$$

$$PTV = DSt \cdot CO, \text{ where } PTV = \text{pulmonary thermal volume}$$

$$GEDV = ITTV - PBV = CO \cdot (MTt - DSt)$$

The present method has limitations in special cases where the site of injection and/or the site of detection cannot be placed near the right atrium or the left ventricle, respectively. As an example, in some patients it is not possible to have the tip of the central venous catheter used for cold indicator injections in the superior vena cava (e.g. subclavian access contraindicated by lung disease or coagulation abnormalities, or jugular venous access contraindicated by local infectious or thrombotic process, or because the site of insertion is within a burned area). In this case, an inferior vena cava catheter must be used for cold indicator injections. When the thermal indicator is injected through an inferior vena cava catheter, usually a femoral venous catheter, the volume of blood between the site of injection and the right atrium is an additional volume of distribution for the cold indicator. As a result, when using a femoral venous access for cold indicator injections, the mean transit time MTt and hence the GEDV are artificially increased. Because normal range for GEDV has been defined from superior vena cava measurements, measuring GEDV by using a femoral venous catheter leads to an overestimation of patient volume status. In this regard, hypovolemic patients may be incorrectly considered as normovolemic, and normovolemic patients may be incorrectly considered as hypervolemic. Since both hypervolemia and hypovolemia are pathologic situations, they frequently lead to therapeutic decisions. Therefore, assessing GEDV by using a femoral venous catheter may lead to incorrect therapeutic interventions and harm to the patients.

Further, the present method according to the prior art does not allow an estimation of true cardiac filling volume (CFV) or (synonyms: true cardiac blood volume (CBV) or true heart end-diastolic volume (HEDV)). Indeed, the GEDV is dependent on CFV, but also on the volume of blood contained between the aortic valve and the site of detection, usually the tip of a femoral arterial catheter. The aortic blood volume may vary from one patient to another according to age, sex, height, weight, total blood volume, and blood pressure. Aortic aneurysms (cylindrical, conical, or sacular) are also responsible of significant variations in aortic blood volume, and further exaggerate the discrepancy between GEDV and CFV or HEDV.

Further the present method according to prior art does not allow an estimation of true cardiac filling volume (CFV) in patient where indicator injection is done
a) either into an extracorporeal subcirculation like into the tubing re-delivering blood to the patient from an e.g. hemodialysis machine (or renal-replacement machine or artificial liver support machine or other extracorporeal circulations) into the venous system,
or
b) directly into a surgically created arterio-venous shunt e.g. at the forearm of the patient.

Especially in chronic hemodialysis patients with an arterio-venous shunt at an extremity the appearance and mean transit time errors caused by varying shunt flow can be tremendous: Efferent shunt flow which is transporting arterial blood from the aorta to the site of puncture for blood withdrawal (by the respective machine) and back from the site of puncture for blood re-delivery to the vena cava may vary between e.g. 300 ml/min to even 1.500 ml/min in adult patients with a forearm shunt.

Thus, it is an object of the invention to propose a method and a device for dilution measurements with which the disadvantages of the prior art can be avoided.

The object of the invention is achieved with a method and an apparatus according to the independent claims. Advantageous features and embodiments are defined in the dependent claims.

The object of the invention is especially achieved with a method for dilution measurements of a central volume (V1) with a first site (S1) of injection of an indicator upstream of the central volume (V1) and a second site (S2) of detection of the diluted indicator downstream of the central volume (V1), wherein a first additional volume (V2) is defined between the first site (S1) and the central volume (V1) through which the indicator flows before entering the central volume (V1) and a first additional branch (B2) is defined between the first site (S1) and the central volume (V1) through which no indicator flows before entering the central volume (V1) but which is connected to the central volume (V1) and wherein a second additional volume (V3) is defined between the central volume (V1) and the second site (S2) through which the indicator flows before entering the second site (S2) and a second additional branch (B3) is defined between the central volume (V1) and the second site (S2) through which (a predefined amount of) indicator flow is branched off and is not entering the second site (S2), wherein a result of central volumetric calculations is corrected for the first and/or second additional volumes (V2, V3) and/or for the first and/or second additional branches (B2, B3) or the delays within the first and/or second additional branches (B2, B3), respectively.

With this method it is possible to provide a corrected parameter for central volumetric calculations, especially a corrected mean or median transit time. With this method, errors introduced by significant volumes and delays within the various branches of the circulation can be calculated and eliminated to obtain the pure central cardiopulmonary volumes of interest. Indicator dilution measurements can now also be performed in remote branches with the desired precision. The method is demonstrated for a single volume and delay in an input and output branch. But the method could be repeated consecutively for multiple branches or multiple volumes or delays. Thus, the invention provides for a method or device for indicator dilution measurements, which corrects the results of central volumetric calculations for volumes and delays within branches caused either by physiological flow in these branches or by flow which is caused by a special surgically created condition like an arterio-venous shunt.

The central volume is the volume of interest for the measurements. The volumes involved upstream and/or downstream the central volume can be estimated, measured, etc. For instance, when a thermal indicator is injected through an inferior vena cava catheter, usually a femoral venous catheter, the volume of blood between the site of injection and the right atrium is an additional volume of distribution for the cold indicator. The volumes can be derived from anthropometric data, that is data about the age, height, weight, gender, etc., and aortic pressure can be monitored continuously. As an alternative, the volumes can be obtained from echography or tomodensitometry or magnetic resonance imaging measurements. As another alternative the volumes involved can be obtained directly from tables or nomograms based on anthropometric data (such as age, height, weight, gender, etc.).

It might also be the case that the site of injection is near the central volume but the site of detection is more remote or vice versa. Thus, the first additional volume might be negligible or even zero whereas the second additional volume is significant and can be used to correct the parameters for central volumetric calculations.

The branches and the flow within the branches can be estimated, measured, etc. At the site of injection, the thermal indicator is introduced and at the site of detection, the response of this indicator is measured. It might now be the case that between the site of injection and the central volume to be measured another branch enters and contributes to the overall flow through the central volume. Thus, the indicator comes from one branch and mixes with flow from another branch not containing any indicator before entering the central volume. For example, a similar situation may arise downstream the central volume. In this case, the flow downstream the central volume may be branched off in one branch flowing through the site of detection and another branch which is deviated and never flows to the site of detection.

With the consideration of additional volumes between the site of injection and the central volume and/or the central volume and the site of detection, additional dilution and time delays introduced can be corrected for or eliminated, respectively.

With the consideration of additional branches between the site of injection and the central volume or the central volume and the site of detection, further additional dilution and time delays introduced can be corrected for or eliminated, respectively.

This method can be carried out with a device which is designed to calculate these parameters and is adapted to correct the values calculated for these additional volumes and/or branches.

In a preferred embodiment of the invention, the dilution measurement is a thermodilution measurement, a dye dilution measurement, a lithium chloride dilution measurement, a density dilution measurement, a dilution measurement with any indicator including a radio-labelled indicator or magnetic resonance detectable indicator which stays intravascularly or also diffuses into the extravascular space in the lungs or any combination thereof, e.g. a thermal dye or thermal lithium measurement, but is close to be completely recovered after the cardio-pulmonary passage.

In a preferred embodiment of the invention, the central volume is the volume of the heart and the lung. Especially, the central volume is the volume of blood contained in the four heart chambers and the lung.

In a preferred embodiment of the invention, the correction takes into account the central flow (Q1) through the central volume (V1), a first additional flow (Q2) within the first additional branch (B2) and/or a second additional flow (Q3) within the second additional branch (B3), wherein the central flow (Q1) is equal to the sum of the first additional flow (Q2) and a first flow (Q2') at the first site of injection (S1) and wherein the central flow (Q1) is equal to the sum of the second additional flow (Q3) and a second flow (Q3') at the second site of detection (S2).

Thus, the flow through the overall system is considered and flows which contain indicator upstream the central volume are defined next to a flow upstream the central volume that does not contain any indicator before entering the central volume. Further or alternatively, a flow through the site of detection is discriminated from a second flow downstream the central volume not passing the site of detection. Thus, errors introduced in the measurements of the prior art are avoided.

In a preferred embodiment of the invention, the correction takes into account the relative flows (rQ) in the different branches, wherein the relative first flow (rQ2') is the quotient of the first flow (Q2') and the central flow (Q1), the relative first additional flow (rQ2) is the quotient of the first additional flow (Q2) and the central flow (Q1), the relative second flow (rQ3') is the quotient of the second flow (Q3') and the central flow (Q1), and the relative second additional flow (rQ3) is the quotient of the second additional flow (Q3) and the central flow (Q1), In a preferred embodiment of the invention, the correction takes into account a theoretical system for which the system output is calculated by applying the convolution to a hypothetical unbranched model with a total flow (Q) and a first, a second and a third apparent volume (W1, W2, W3), wherein the first apparent volume (W1) is the central volume (V1), the second apparent volume (W2) is the quotient of the first additional volume (V2) and the relative first flow (rQ2') and the third apparent volume (W3) is the quotient of the second additional volume (V3) and the relative second flow (rQ3'). The apparent volumes take into account the correction for the additional volumes and the branches involved. Thus, with this model, the calculation of the corrected values can be carried out on a simpler set up.

Especially, a method for data gathering and/or data processing is provided determining the cardiac filling volume (CFV), or cardiac blood volume (CBV) or heart end-diastolic volume (HEDV) of a subject instrumented with a central venous catheter and an arterial catheter,
a) using indicator dilution, preferably thermodilution
b) injecting a cold bolus into the central venous catheter
c) detecting of the thermodilution curve with an arterial catheter
d) measuring the total mean transit time from the point of injection to the point of detection, or alternatively,
e) correcting the total mean transit (d) for the additional appearance time error caused by the travel of the thermal indicator from the site of injection to the right atrium,
f) further correcting the total mean transit (d) for the appearance time error caused by the additional travel of the thermal indicator from the aortic valve to the site of detection,
g) calculating cardiac output and down-slope time from the thermodilution curve
h) using the corrected mean transit according to e), cardiac output, and down-slope time, in order to obtain CFV (or CBV or HEDV).

In a preferred embodiment of the present application the first additional volume (V2) and/or the second additional volume (V3) comprises a hemodialysis shunt and/or a hemodialysis machine and/or at least a part of an extracorporeal circuit. Thus, it is possible to consider the errors in a hemodialysis or any other arterio-venous extracorporeal set-up and correct them according to the present invention.

The object of the invention is also achieved by a device for indicator dilution measurements of a central volume (V1) with a processor (P) and a first input means (I1) for receiving data from a first site of injection (S1) of an indicator upstream of the central volume (V1) and a second input means (I2) for receiving data from a second site of detection (S2) of the diluted indicator downstream of the central volume (V1), wherein a first additional volume (V2) is defined between the first site (S1) and the central volume (V1) through which the indicator flows before entering the central volume (V1) and a first additional branch (B2) is defined between the first site (S1) and the central volume (V1) through which no indicator flows before entering the central volume (V1) but which is connected to the central volume (V1) and wherein a second additional volume (V3) is defined between the central volume (V1) and the second site (S2) through which the indicator flows before entering the second site (S2) and a second additional branch (B3) is defined between the central volume (V1) and the second site (S2) through which a predefined amount of indicator flow is branched off and is not entering the second site (S2) wherein the processor is adapted to perform calculations for a result of central volumetric parameters and these calculations are corrected for the first and second additional volumes (V2, V3) and/or for the first and second additional branches (B2, B3).

With this device it is possible to provide a corrected parameter for central volumetric calculations, especially a corrected mean or median transit time. With this device, errors introduced by significant volumes and delays within the various branches can be calculated and eliminated to obtain the pure central volumes of interest. Dilution measurements now can also be performed in remote branches with the desired precision.

As a processor any means for calculation can be used, preferably integrated in a bedside monitor.

As first input means for receiving data from a first site of injection of an indicator upstream the central volume different sensors can be used. Preferably, a thermal sensor is used to measure the temperature of the indicator. Additionally, a time measurement means is used to measure the time of injection. Further, a pressure sensor can be used to measure the pressure as an indicator of the start and end time of the injection process of the indicator. Further, a volume measurement means can be employed to measure the amount of indicator injected. It might also be possible to use a predefined amount of injectate and to input this value into the processor beforehand.

As second input means for receiving data from a second site of detection of the diluted indicator downstream the central volume, preferably a thermal sensor is used to record the temperature and the change of temperature in the stream containing the indicator after passing the central volume. Preferably, a time measurement means is employed to measure the time delay between the injection and the detection.

The processor is adapted to perform calculations for a result of central volumetric parameters, i.e. to calculate cardiac output (CO) and global end-diastolic volume (GEDV). Further, the processor is adapted to perform calculations that are corrected for the first and second additional volumes and/or for the first and second additional branches. Thus, the processor or device is adapted to calculate the true cardiac filling volume (CFV) or—synonyms—true cardiac blood volume (CBV) or true heart end-diastolic volume (HEDV), respectively.

In a preferred embodiment of the invention, the device is adapted to carry out one or more of the methods according to the invention.

The invention is now described with respect to further examples that contain advantageous embodiments of the present invention.

EXAMPLES

This invention also describes a new method and apparatus for estimating the volume of blood contained in the four heart chambers, called Cardiac Filling Volume (CFV) or Cardiac Blood Volume (CBV) or Heart End-Diastolic Volume (HEDV).

This method is based on the measurement of cardiac output and mean transit time MTt of the cold indicator according to previous art, and on the calculation of a corrected mean transit time cMTt. The corrected transit time cMTt is the mean transit time MTt corrected by the introduced appearance time errors which result from the transport time of the indicator from the site of injection to the right atrium and from the transport of the thermal indicator from the aortic valve to the detection site.

Example 1

When the central venous catheter is femoral, the appearance time error from the site of injection to the right atrium $ATE_{pre}$ can be calculated as:

$$ATE_{pre} = (D_{ivc}/2)^2 \cdot \Pi \cdot L_{si-ra}/(a \cdot CO)$$

where $ATE_{pre}$=pre-cardiac appearance time error,
$D_{ivc}$=diameter of the inferior vena cava,
$L_{si-ra}$=vessel length from site of injection to right atrium,
CO=cardiac output,
a=percentage of cardiac output passing through the inferior vena cava, which is commonly known to account for 65-70% of CO.

The diameter of the inferior vena cava $D_{ivc}$ is mainly dependent on inferior vena cava pressure or central venous pressure CVP and can be estimated as $D_{ivc}$=f (CVP). The relationship between CVP and $D_{ivc}$ is curvilinear.

For example, $D_{ivc}$ can be calculated as: $D_{ivc}$=1.85·CVP−0.03 $CVP^2$ such that $D_{ivc}$ will range from 0 cm to 2.85 cm when CVP ranges from 0 to 30 mmHg.

As an alternative the inferior vena cava diameter can be obtained from echography or tomodensitometry or magnetic resonance imaging measurements.

The vessel length from the site of injection to the right atrium $L_{si-ra}$ is mainly dependent on the height H of the patient and can be estimated as $L_{si-ra}$=f (H). For example, $L_{si-ra}$ can be estimated as $L_{si-ra}$=0.18·H.

Example 2

When the arterial catheter is femoral (usual case), the appearance time error from the aortic valve to the site of detection can be calculated as:

$$ATE_{post} = [(D_{ao}/2)^2 \cdot \Pi \cdot L_{av-fa}]/(b \cdot CO)$$

where
$ATE_{post}$=post-cardiac appearance time error
$D_{ao}$=aortic diameter
$L_{av-fa}$=vessel length from aortic valve to site of detection with femoral artery catheter
b=percentage of cardiac output passing through the descending aorta, usually estimated at 65-70%.

The aortic diameter $D_{ao}$ is mainly dependent on aortic compliance and aortic pressure. Aortic compliance can be derived from anthropometric data, that is data about the age, height, weight, gender, etc., and aortic pressure can be monitored continuously.

As an alternative the aortic diameter $D_{ao}$ can be obtained from echography or tomodensitometry or magnetic resonance imaging measurements.

As another alternative the aortic diameter $D_{ao}$ can be obtained directly from tables or nomograms based on anthropometric data (such as age, height, weight, gender, etc.).

The vessel length from aortic valve to site of detection $L_{av-sd}$ with the femoral artery catheter is mainly dependent on patient height H and can be estimated as $L_{av-fa}$=f (H). For example, $L_{av-fa}$ can be estimated as $L_{av-fa}$=0.23·H.

As an alternative, in patients with cylindrical aortic aneurysm, $ATE_{post}$ can be calculated as:

$$ATE_{post} = [(D_{ao}/2)^2 \cdot \Pi \cdot (L_{av-fa} - L_{aa}) + (D_{aa}/2)^2 \cdot \Pi \cdot L_{aa}]/(b \cdot CO)$$

where
$D_{aa}$=maximum diameter of the aortic aneurysm, obtained from echography or tomodensitometry or magnetic resonance imaging or angiography measurements
$L_{aa}$=length of the aortic aneurysm, obtained from echography or tomodensitometry or magnetic resonance imaging or angiography measurements.

In case of abdominal aortic aneurysm in adults within the height H range 142-191 cm, $L_{aa}$ can also be estimated at 90 mm which is the distance from the renal arteries to the iliac bifurcation.

As another alternative, in patients with conical aortic aneurysm, $ATE_{post}$ can be calculated as:

$$ATE_{post} = [(D_{ao}/2)^2 \cdot \Pi \cdot (L_{av-fa} - L_{aa}) + (D_{aa}/2)^2 \cdot \Pi \cdot L_{aa}/3]/(b \cdot CO)$$

As another alternative, in patients with sacular aortic aneurysm, $ATE_{post}$ can be calculated as:

$$ATE_{post} = [(D_{ao}/2)^2 \cdot \Pi \cdot (L_{av-fa} - D_{aa}) + (D_{aa}/2)^3 \cdot \Pi \cdot L_{aa}3]/(b \cdot CO)$$

As another alternative, when the arterial indicator sensing catheter is placed brachially or axillary, the appearance time error from the aortic valve to the site of detection is calculated as:

$$ATE_{post} = [(D_{ao}/2)^2 \cdot \Pi \cdot L_{av-ba}]/(c \cdot CO)$$

where
$L_{av-ba}$=vessel length from aortic valve to site of detection with brachial artery catheter, estimated from $L_{av-ba}$=(H−50)/7.5+5 with H being body height
c=percentage of cardiac output which does not pass through the descending aorta, usually estimated at 30-35%.

Example 3

When indicator injection is performed into the blood re-delivering tubing of an extracorporeal circuit (such as hemodialysis machine) close to puncture site (such as at an forearm arterio-venous shunt) and the indicator dilution curve is detected in the blood withdrawal tubing of the extracorporeal circuit (such as a hemodialysis machine) close to the puncture site, the appearance time error correction preferably consists of several steps:
  a) Correction of the pre-cardiac appearance time error $ATE_{pre}1$ from point of injection in the blood re-delivering tubing to the site of puncture of a blood vessel or a hemodialysis shunt:
  Provided that
    aa) there is no backflow of blood in the tubing to the extracorporeal circuit during indicator injection into the tubing, and
    bb) the volume of the tubing from the point of injection in the tubing to the puncture site $V_t1$ is larger than the injectate volume
  the error is calculated as:

$$ATE_{pre}1 = V_t1/BF_H$$

where $BF_H$=Blood Flow of the extracorporeal circuit (obtained from the machine)
  b) Correction of appearance time error $ATE_{pre}2$ from site of puncture of the blood vessel or hemodialysis shunt to entrance point of the shunt vessel into the vena cava:

in case of a hemodialysis shunt the internal diameter of the surgically created shunt vessel is getting larger in the first weeks after the surgical procedure and before usage of the shunt for hemodialysis caused by the initially high blood flow through and high pressure within the shunt. For purpose of estimation it is assumed that the average diameter $D_s$ of a surgically created shunt usable for hemodialysis is applicable to the whole shunt vasculature from the point of branching off from the aorta to the two puncture sites (withdrawal and re-delivery) and further to the point of re-entering into a large systemic vein like the vena cava superior.

The pre-cardiac appearance time error $ATE_{pre}2$ caused by this "venous" afferent part of the shunt vasculature is calculated as:

$$ATE_{pre}2 = (L_{asv} \cdot Ds)/BF_s$$

where $BFs$=actual blood flow through the hemodialysis shunt
$Ds$=average diameter of shunt vasculature
$BF_s$ and $D_s$ may be obtained from indicator dilution with
bb) reverse hemodynamic pump flow
bc) injection into the tubing normally used for blood withdrawal
bd) detection of the trans-shunt indicator dilution curve in the tubing normally used for re-delivery of blood
be) calculating shunt flow $BF_s$ using basically the Stewart-Hamilton algorithm
bf) correcting for the appearance time errors caused by the indicator flowing through withdrawal and re-delivery tubing using the principles described here
bg) calculating shunt volume Vs between the two puncture sites from the product of $BF_s$ and the appearance time error corrected mean transit time
bh) assuming that the shunt volume $V_s$ is contained in a cylindrical vessel with length $L_s$ identical to the distance of the 2 puncture sites, then $D_s$ is calculated from $$D_s = 2 \cdot \sqrt{\frac{V_s}{L_s \cdot \Pi}}$$

$BF_s$ and $D_s$ may also be obtained from ultrasound examination where basically blood velocity in the shunt and $D_s$ are measured and BF is calculated as the product thereof.

d) Correction of appearance time error $ATE_{pre}3$ from the entrance site of the shunt vessel into the vena cava superior to the right atrium The pre-cardiac appearance time error $ATE_{pre}3$ is calculated from:

$$ATE_{pre}3 = (D_{svc}/2)^2 \cdot \Pi \cdot L_{sevcs-ra}/(d \cdot CO)$$

where $D_{svc}$=diameter of the superior vena cava,
$L_{sevcs-ra}$=vessel length from entrance of shunt vessel into vena cava superior to right atrium,
d=percentage of cardiac output passing through the superior vena cava, which is known to account for 30-35% of CO.

The diameter of the superior vena cava $D_{svc}$ is mainly dependent on superior vena cava pressure or central venous pressure CVP and can be estimated as $D_{svc}$=f(CVP). The relationship between CVP and $D_{svc}$ is curvilinear.

For example, $D_{svc}$ can be calculated in a similar way as $D_{ivc}$ as already mentioned above.

As an alternative the superior vena cava diameter can be obtained from chest X-ray, echography or tomodensitometry or magnetic resonance imaging measurements or clinical estimates.

The vessel length from entrance of shunt vessel into vena cava superior to right atrium $L_{sevcs-ra}$ is mainly dependent on the height H of the patient and can be estimated as $L_{si-ra}$=f(H). For example, $L_{si-ra}$ can be estimated as $L_{si-ra}$=0.09·H.

e) Correction of appearance time error $ATE_{post}1$ from the aortic valve to the site where the shunt vessel branches off from the aorta $$ATE_{post}1 = [(D_{ao}/2)^2 \cdot \Pi \cdot L_{av-sv}]/(c \cdot CO)$$

where $D_{ao}$=aortic diameter
$L_{av-sv}$=vessel length from aortic valve to site of branching off of shunt vessel
c=percentage of cardiac output not passing through the descending aorta known to account for 65-70% of CO.

The aortic diameter $D_{ao}$ can be determined as described above.

The vessel length from aortic valve to site of branching off of shunt vessel $L_{av-sv}$ again is mainly dependent on patient height H and can be estimated as $L_{av-sv}$=f(H). For example, $L_{av-sv}$ can be estimated as $L_{av-sv}$=0.09·H.

f) Correction of the appearance time error $ATE_{post}2$ from point where the shunt vessel branches off from the aorta to the puncture site of the hemodialysis shunt for blood withdrawal by the hemodialysis machine By definition of this model above the afferent part of the total shunt vasculature in terms of vascular volume and flow is identical to the efferent part.

This means that $$ATE_{post}2 = ATE_{pre}2$$

g) Correction of the appearance time error $ATE_{post}3$ in the blood withdrawal tubing from the puncture site to the point of detection of the indicator dilution curve in the tubing according to $$ATE_{post}3 = V_t2/BF_H$$

where $BF_H$=Blood Flow of the hemodialysis machine (obtained from the machine)
$V_t2$=Volume of blood withdrawal tubing from puncture site to site of indicator detection In this Example the corrected cMTt is obtained from $$cMTt = MTt - (ATE_{pre}1 + ATE_{pre}2 + ATE_{pre}3 + ATE_{post}1 + ATE_{post}2 + ATE_{post}3)$$

Alternatively, $ATE_{post}2$ and $ATE_{pre}2$ could be differentiated further applying the same principles as above by assuming that the efferent shunt vessel starts at the level of the axillary or brachial vein and, vice versa, the afferent shunt vessel ends at the level of the axillary or brachial vein respectively.

In all Examples, a corrected appearance time can be calculated by subtracting $ATE_{post}$ and $ATE_{pre}$ from the measured appearance time. A corrected mean transit time cMTt can therefore be calculated from the corrected appearance time and MTt, and cardiac filling volume CFV (or cardiac blood volume CBV or heart end-diastolic volume HEDV) can be calculated as:

$$CFV = CO \cdot (cMTt - DSt) \quad \quad (5)$$

Figure 2:
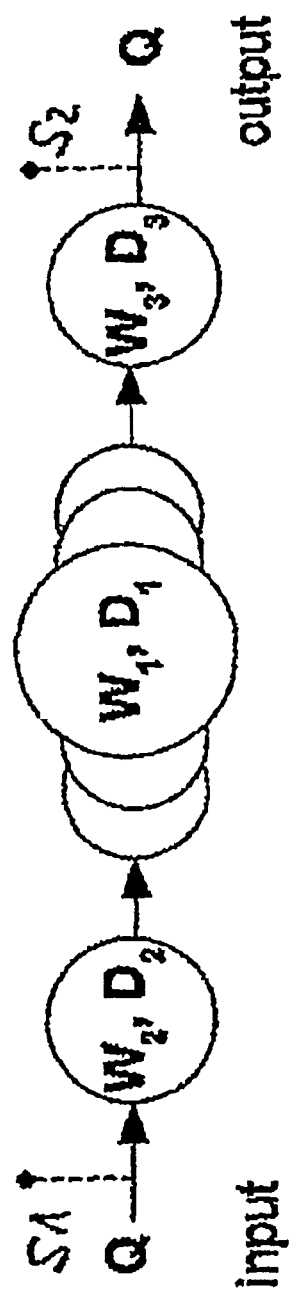
Figure 3:
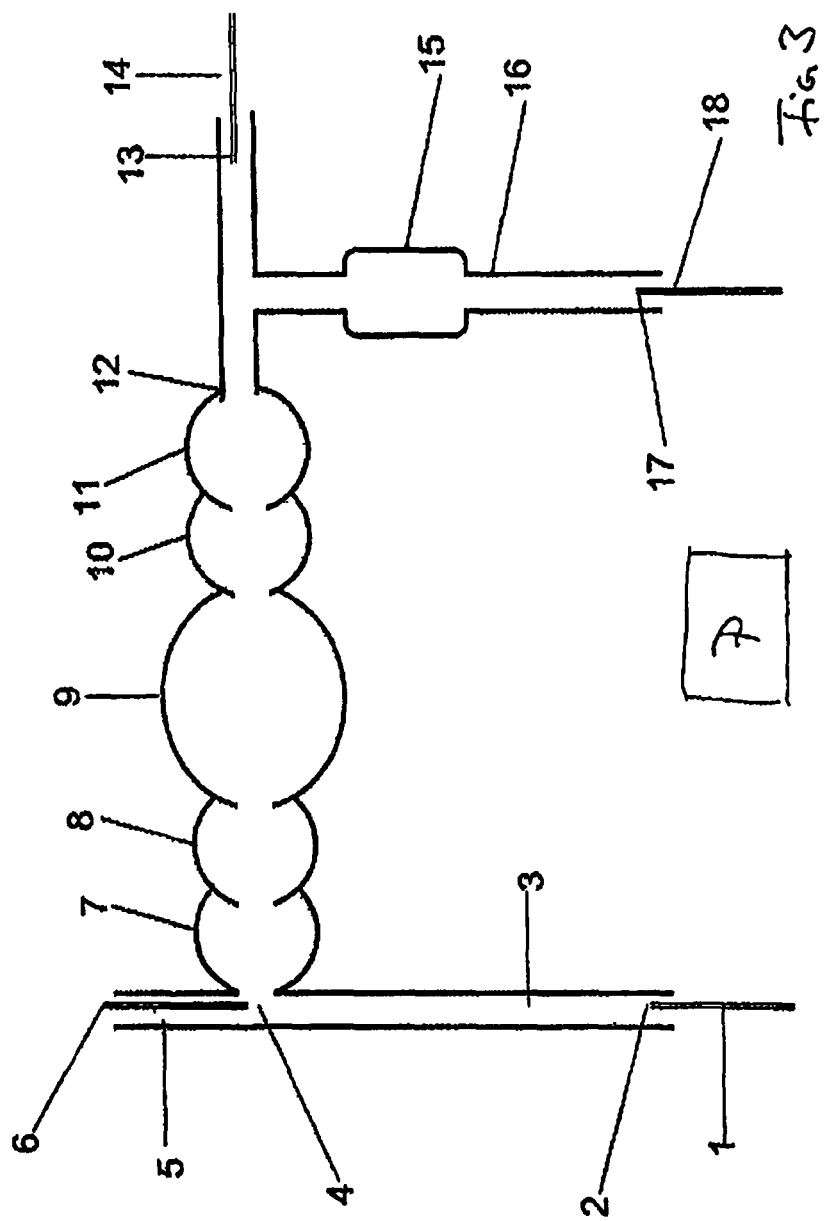
Figure 4:
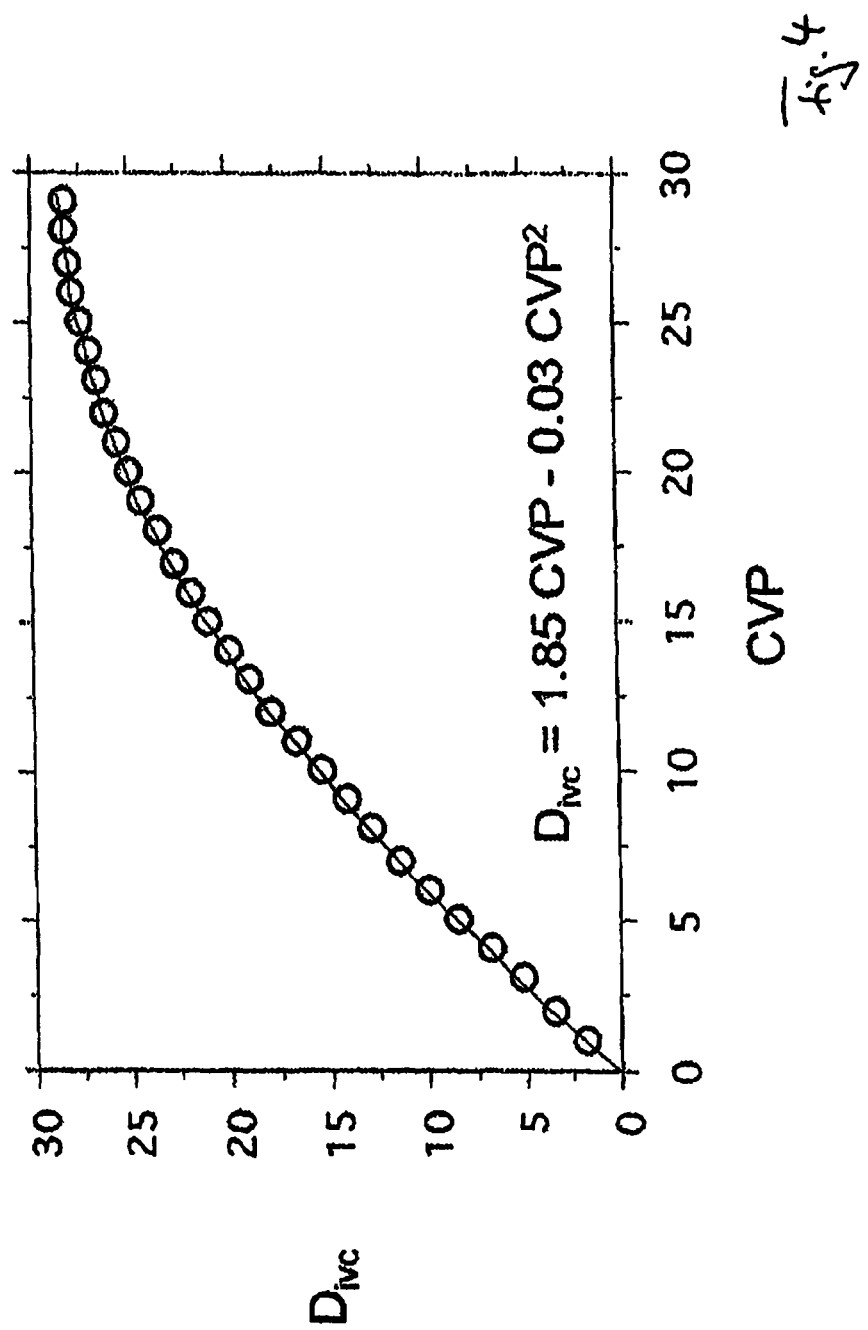
Figure 5:
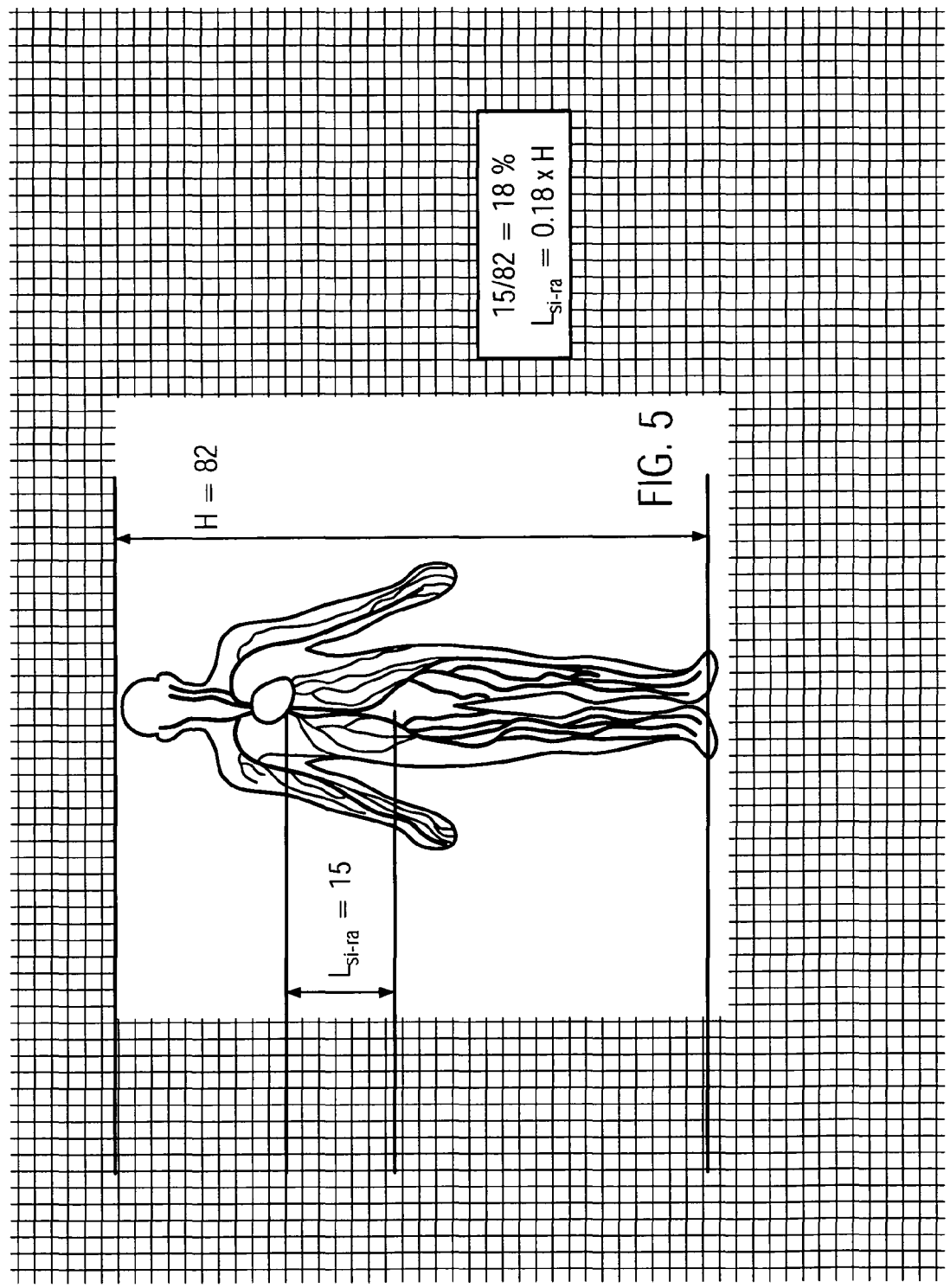
Figure 6:
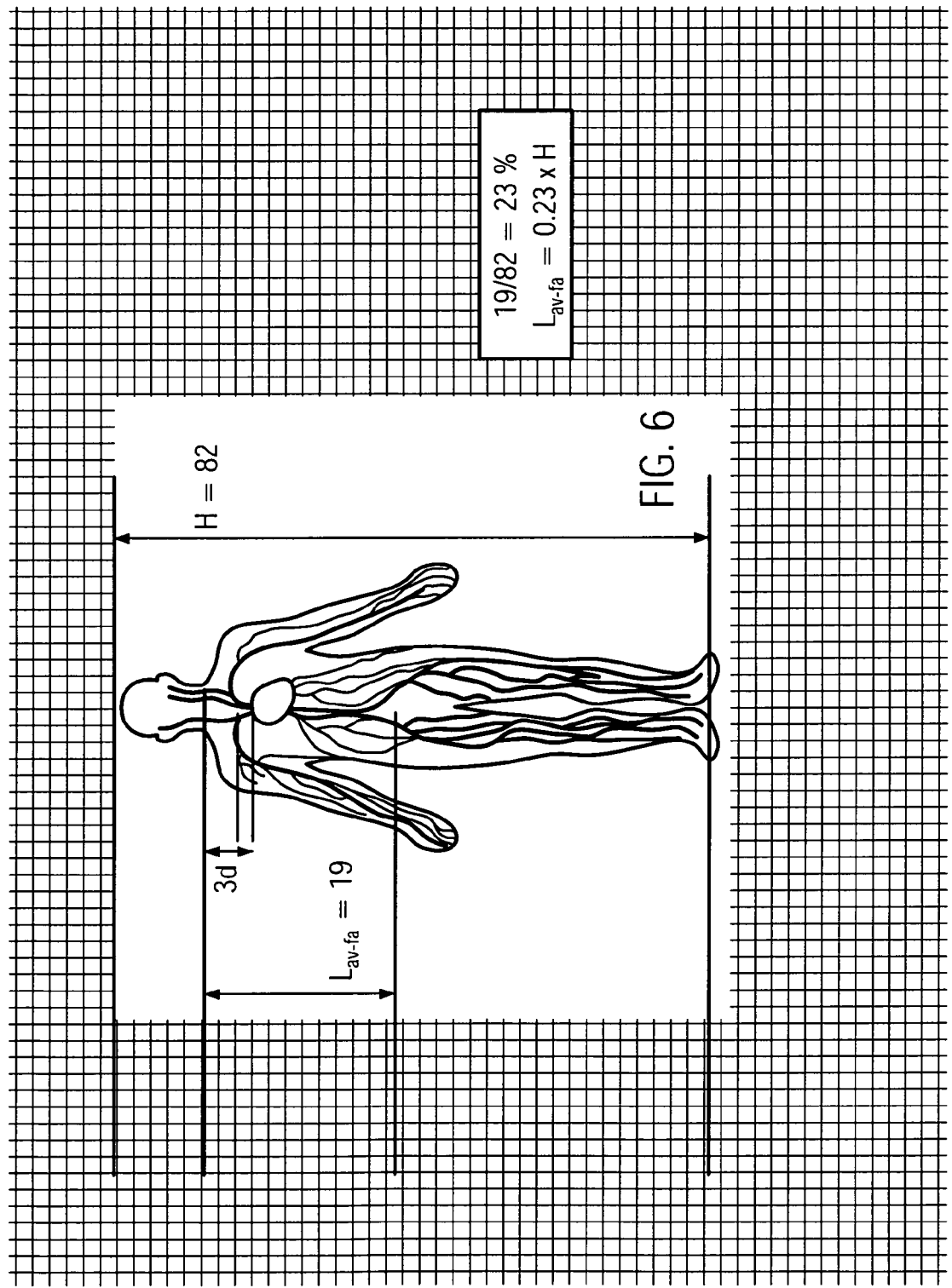

The invention is now illustrated and described with respect to figures containing advantageous embodiments of the invention. The figures show:

FIG. 1 A schematic drawing of the volumes according to one embodiment of the invention;

FIG. 2 A schematic view of a hypothetical unbranched model of FIG. 1 with the total flow Q and the apparent volumes W;

FIG. 3 A schematic view of the volumes and branches according to a thermodilution measurement of cardiac output (CO) and global end-diastolic volume (GEDV);

FIG. 4 A graph for calculating the diameter of the inferior vena cava $D_{ivc}$;

FIG. 5 A schematic view for illustrating the calculation of the vessel length from the site of injection to the right atrium $L_{si-ra}$; and FIG. 6 Another schematic view for illustrating the calculation of the vessel length from the aortic valve to the site of detection $L_{av-sd}$.

In FIG. 1 a schematic drawing of the volumes according to one embodiment of the invention is shown. A central Volume V1 which consists of several subvolumes and a respective delay D1 associated to the central volume V1 is shown schematically with five circles representing for instance a heart chamber system. Upstream the central volume, a first site of injection S1 is shown. Between the site of injection S1 and the central volume V1, a first additional volume V2 and a respective first additional delay D2 is indicated. The flow through the site of injection S1 is designated with Qxa. A first additional branch B2 with an additional flow Qxb is shown that enters the central volume V1 without passing the site of injection S1. Downstream the central volume V1, a second site of detection S2 is shown. Between the central volume V1 and the site of detection S2, a second additional volume V3 is shown with a respective second delay D3 associated to the volume V3. A flow Qya is shown to pass the site of detection S2. A second additional branch B3 is shown having an additional flow Qyb.

The indicator is injected before V2 and the response is detected after V3. It is assumed that the two input flows Qxa, Qxb result in a single total flow Q within the central volume V1, which is divided again into two branches with flows Qya, Qyb.

$$Q = Q_{xa} + Q_{xb} = Q_{ya} + Q_{yb}$$

Thus, the relative flows are defined:

$$q_{xa} := \frac{Q_{xa}}{Q}; \quad q_{xb} := \frac{Q_{xb}}{Q}; \quad q_{ya} := \frac{Q_{ya}}{Q}; \quad q_{yb} := \frac{Q_{yb}}{Q}$$

In FIG. 2 a schematic view of a hypothetical unbranched model of FIG. 1 with the total flow Q and the apparent volumes W is shown.

The system output is for instance calculated by applying the convolution to a hypothetical unbranched model with the total flow Q and the apparent volumes W $$W_1 := V_1; \quad W_2 := \frac{V_2}{q_{xa}}; \quad W_3 := \frac{V_3}{q_{ya}}$$

The delay times will be unaffected by this procedure and would result in a total time shift of the dilution curve. The system output would be $$y_a(t + t_{d1} + t_{d2} + t_{d3}) = \frac{X_a(t)}{Q} * (W_2 * W_1 * W_3)$$

with the time constants $$\tau_1 = \frac{W_1}{Q} = \frac{V_1}{Q}; \quad \tau_2 = \frac{W_2}{Q} = \frac{V_2}{q_{xa}Q}; \quad \tau_3 = \frac{W_3}{Q} = \frac{V_3}{q_{ya}Q};$$

and a bolus injection of the indicator quantity $X_a$, which results in $$y_a(t + t_{d1} + t_{d2} + t_{d3}) =$$

$$\frac{X_a}{Q} \left[ \frac{\tau_1 e^{-t/\tau_1}}{(\tau_1 - \tau_2)(\tau_1 - \tau_3)} + \frac{\tau_2 e^{-t/\tau_2}}{(\tau_2 - \tau_1)(\tau_2 - \tau_3)} + \frac{\tau_3 e^{-t/\tau_3}}{(\tau_3 - \tau_2)(\tau_3 - \tau_1)} \right]$$

All volumes $V_n$ within the different branches seem to be enlarged by the inverse of the respective relative flow $q_n$. Therefore the volumes are weighted by the inverse relative flow.

E.g. a 10 ml volume in a sub branch of 25% flow will be treated as a 40 ml unbranched apparent volume. The multiple branched dilution can now be calculated like a single input, single output dilution. If the volumes and delays and sub flows within the sub branches are measured or known, the result can be corrected accordingly.

The apparent volume $W_i$ could be used to estimate the according transfer function—a monoexponential decay with time constant $\tau_i$. E.g. Applying an appropriate Wiener filter, the dilution curve could be deconvoluted with this transfer function in order to reconstruct the dilution curve without this volume.

In case of a single small apparent volume $W_i$ compared to the sum of all apparent volumes, the effect of this volume could be approximated by an additional delay time $$t_i = \tau_i = \frac{W_i}{Q}$$

In FIG. 3 a schematic view of the volumes and branches according to a thermodilution measurement of cardiac output (CO) and global end-diastolic volume (GEDV) is shown.

A femoral venous catheter 1 is placed at a site of cold indicator injection 2 in the inferior vena cava 3 remote to the entrance of the right atrium 4. A subclavian or jugular venous catheter 6 is placed in the superior vena cava 5 in the vicinity of the right atrium 7. The right atrium 7 is followed by the right ventricle 8, the pulmonary thermal volume 9 (pulmonary blood volume+extravascular lung water), the left atrium 10 and the left ventricle 11. The aortic valve 12 is followed by the aorta which is branched off into the axillary artery and the descending aorta 16. Two alternative sites of detection are shown: a site of detection of the thermodilution curve (brachial or axillary arterial catheter) 13 with a brachial or axillary thermistor-tipped arterial catheter 14 and a site of detection of the thermodilution curve (femoral arterial catheter) 17 with a femoral thermistor-tipped arterial catheter 18. An aortic aneurysm 15 is shown in the descending aorta 16. A processor P is shown to which the signals from the sensors 1, 6, 14 and 18 are fed.

According to an embodiment of the invention, the dilution measurement is corrected for the additional volumes and branches dependent on which sensors are used for the measurement. The central volume to be measured is the sum of the volumes 7, 8, 9, 10 and 11. In case the subclavian or jugular venous catheter 6 is used for injecting the indicator directly in front of the right atrium, no volumes upstream the central volume has to be considered. However, in case the femoral venous catheter 1 is used to inject the indicator, the volume of the inferior vena cava 3 from the site of cold indicator injection 2 until the right atrium 4 is considered as a first additional volume. Further, the flow from the superior vena cava 5 entering the right atrium 4 mixes with the flow from the vena cava 3 containing the indicator. Thus, this additional flow through the superior vena cava 5 is considered and compensated for.

Further, downstream the central volume two sites of detection 13 and 17 are shown. In case the brachial or axillary thermistor-tipped arterial catheter 14 at the site 13 is used, the additional volume between the aortic valve 12 and the site 13 can be considered.

The flow downstream the central volume, i.e. downstream the aortic valve 12 is branched off into the axillary aorta and the descending aorta 16. Thus, the flow in the descending aorta 16 also containing indicator does not reach the site of detection 13. According to the invention, the processor corrects for this additional branch or the flow not reaching the site 13, respectively. In case that the site 17 is used as a site for detection, the branch and flow into the axillary aorta is not reaching the site of detection 17 and is compensated for. Further, the additional volume between the aortic valve 12 and the site 17 is taken into account. On one hand, this is the volume of the descending aorta 16, on the other hand, it is the aortic aneurysm 15 in the descending aorta 16. Thus, the errors incurred by using the site 17 for measurement can be corrected.

In FIG. 4 a graph for calculating the diameter of the inferior vena cava $D_{ivc}$ is shown. This graph describes how, based on clinical validation against ultrasound determinations, the diameter of the inferior vena cava $D_{ivc}$ may be obtained just from measurements of central venous pressure.

The diameter of the inferior vena cava $D_{ivc}$ is mainly dependent on inferior vena cava pressure or central venous pressure CVP and can be estimated as $D_{ivc}=f(CVP)$. The relationship between CVP and $D_{ivc}$ is curvilinear.

For example, $D_{ivc}$ can be calculated as: $D_{ivc}=1.85\ CVP-0.03\ CVP^2$ such that $D_{ivc}$ will range from 0 cm to 2.85 cm when CVP ranges from 0 to 30 mmHg.

In FIG. 5 a schematic view for illustrating the calculation of the vessel length from the site of injection to the right atrium $L_{si-ra}$ is shown. The vessel length from the site of injection to the right atrium $L_{si-ra}$ is mainly dependent on the height H of the patient and can be estimated as $L_{si-ra}=f(H)$. For example, $L_{si-ra}$ can be estimated as $L_{si-ra}=0.18 \cdot H$.

In FIG. 6 another schematic view for illustrating the calculation of the vessel length from the aortic valve to the site of detection $L_{av-sd}$ is shown. The vessel length from aortic valve to site of detection $L_{av-sd}$ with the femoral artery catheter is mainly dependent on patient height H and can be estimated as $L_{av-fa}=f(H)$. For example, $L_{av-fa}$ can be estimated as $L_{av-fa}=0.23 \cdot H$.

Thus, it is provided a method and an apparatus for a more reliable estimation of the true cardiac filling volume (CFV) or true cardiac blood volume (CBV) or true heart end-diastolic volume (HEDV), respectively.

REFERENCE SIGNS

1 femoral venous catheter
2 site of cold indicator injection
3 inferior vena cava
4 entrance of the right atrium
5 superior vena cava
6 sub-clavian or jugular venous catheter
7 right atrium
8 right ventricle
9 pulmonary thermal volume (pulmonary blood volume+ extravascular lung water)
10 left atrium
11 left ventricle
12 Aortic valve
13 site of detection of the thermodilution curve (brachial or axillary arterial catheter)
14 brachial or axillary thermistor-tipped arterial catheter
15 Aortic aneurysm
16 descending aorta
17 site of detection of the thermodilution curve (femoral arterial catheter)
18 femoral thermistor-tipped arterial catheter

The invention claimed is:

1. A method for correcting a dilution-based determination of an internal volume of a heart based on flow of a diluted indicator between an injection site upstream of the heart and a detection site downstream of the heart, the method comprising:
    injecting indicator at the injection site;
    diluting the injected indicator in blood flowing through the heart between the injection site and the detection site;
    detecting diluted indicator at the detection site; and
    operating a processor configured to carry out the steps of:
        calculating the internal volume of the heart based on a detection of the diluted indicator at the detection site;
        estimating an additional volume through which the injected indicator flows, the estimated additional volume being estimated as substantially an entire internal volume of a blood vessel through which the injected indicator flows between the injection site and the entrance to the right atrium of the heart; and
        calculating and applying a correction to calculation of the internal volume of the heart based on the estimated additional volume.

2. A method for correcting a dilution-based determination of an internal volume of a heart based on flow of a diluted indicator between an injection site upstream of the heart and a detection site downstream of the heart, the method comprising:
    injecting indicator at the injection site;
    diluting the injected indicator in blood flowing through the heart between the injection site and the detection site;
    detecting diluted indicator at the detection site; and
    operating a processor configured to carry out the steps of:
        calculating the internal volume of the heart based on a detection of the diluted indicator at the detection site;
        estimating an additional volume through which the injected indicator flows, the estimated additional volume being estimated as substantially an entire internal volume of a blood vessel through which the injected indicator flows between the aortic valve and the detection site; and calculating and applying a correction to the calculation of the internal volume of the heart based the estimated additional volume.

3. A method for correcting a dilution-based determination of an internal volume of a heart based on flow of a diluted indicator between an injection site upstream of the heart and a detection site downstream of the heart, the method comprising:

injecting indicator at the injection site;
diluting the injected indicator in blood flowing through the heart between the injection site and the detection site;
detecting diluted indicator at the detection site; and
operating a processor configured to carry out the steps of:
calculating the internal volume of the heart based on a detection of the diluted indicator at the detection site; and
calculating and applying a correction to the calculation of the internal volume of the heart based on an estimated flow of blood in a branch through which no indicator flows but through which blood flows upstream of the heart before entering the heart.

4. A method for correcting a dilution-based determination of an internal volume of a heart based on flow of a diluted indicator between an injection site upstream of the heart and a detection site downstream of the heart, the method comprising:

injecting indicator at the injection site;
diluting the injected indicator in blood flowing through the heart between the injection site and the detection site;
detecting diluted indicator at the detection site; and
operating a processor configured to carry out the steps of:
calculating the internal volume of the heart based on the detection of the diluted indicator at the detection site; and
calculating and applying a correction to the calculation of the internal volume of the heart based on an estimated flow of blood in a branch downstream of the heart and through which indicator flows but not past the detection site.

* * * * *